United States Patent
Soong

(10) Patent No.: US 6,783,774 B1
(45) Date of Patent: *Aug. 31, 2004

(54) SUBSTANCE THAT STOP ANY KIND OF BLEEDING WITHIN ONE SECOND FOR MEDICAL, SURGICAL, POSTSURGICAL AND DENTAL USES

(75) Inventor: Leslie Binshyang Soong, San Francisco, CA (US)

(73) Assignee: Leslie B. Song, San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/354,653

(22) Filed: Dec. 13, 1994

Related U.S. Application Data

(63) Continuation-in-part of application No. 08/139,343, filed on Oct. 20, 1993, now abandoned, which is a continuation of application No. 07/760,514, filed on Aug. 29, 1991, now abandoned, which is a continuation-in-part of application No. 07/624,094, filed on Dec. 6, 1990, now abandoned.

(51) Int. Cl.$^7$ .............................. A61K 9/14; A61K 9/48; A61K 9/66
(52) U.S. Cl. ....................... 424/489; 424/451; 424/455; 514/834
(58) Field of Search ................................ 424/489, 464, 424/451, 456, 455

(56) References Cited

PUBLICATIONS

Current Medical Diagnosis & Treatment 1981, p. 341. Authors; Marcus A. Krupp & Milton J. Chatton.
Loukas, YL, Journal of Pharmaceutical and Biomedical Analysis, May 1998, 17(1):133–40.
Peter M. Collins, 1998, Dictionary of Carbohydrate, Chapman & Hall, p. 133.
Crawfords, 1980, Adv. Carbohy. Chem. Biochem., vol. 37, 82–84 Forsberg, O. et al, Chem. Scripta 1973, 3, 153–158.

*Primary Examiner*—James M. Spear

(57) ABSTRACT

There is disclosed a method for stopping bleeding and forming black blood coagulation on contact, comprising administering powdered L-threo-hex-2-enono-1,4-lactone thereof to a bleeding site in an amount of 0.1568 grams for every milliliter of blood. This includes cancer, liver diseases and hemophiliac bleeding in patients or animals in whom the thrombocytopenia or coagulation factors disorders result. Accordingly, the said mechanism of action of powdered L-threo-hex-2-enono-1,4-lactone in the formation of blood coagulation on contact is the unique common pathway for all blood coagulations, which overturns the mechanisms of intrinsic and extrinsic pathways for blood coagulation cascade being the unique pathways for blood coagulation in which the coagulation factors 1, 2, 5, 7, 8, 9, 10 and platelet factor 3 are essential for the pathways.

20 Claims, No Drawings

SUBSTANCE THAT STOP ANY KIND OF BLEEDING WITHIN ONE SECOND FOR MEDICAL, SURGICAL, POSTSURGICAL AND DENTAL USES

CROSS REFERENCE RELATED TO APPLICATION

This application is a continuation-in-part of U.S. application Ser. No. 08/139,343, filed Oct. 20, 1993 now Abandoned, which application was a continuation of U.S. application Ser. No. 07/760,514, filed Aug. 29, 1991, Abandoned which application was a continuation-in-part of U.S. application Ser. No. 07/624,094 filed Dec. 6, 1990, now abandoned.

BACKGROUND OF THE INVENTION

The present invention pertains to the field of blood coagulation, which is further related to evaluation of coagulation tests; e.g. prothrombin time, partial thromboplastin time and activated partial thromboplastin time etc., and coagulation factor disorders. However, the blood coagulation mechanism of action of powdered D,L-threo-hex-2-enono-1,4-lactone which was administered topically does not fall into either intrinsic or extrinsic pathway cascade of blood coagulation scheme, since it works the same for blood coagulation in normal situation as in chronic hepatitis, colon cancer, and hemophilia patients in whom the coagulation factors 1, 2, 5, 7, 9, 10 and platelets in the liver disease and factor 8 or 9 in the hemophilia A or B are abnormal, or suppressed the syntheses, and destroyed and deficient (Harrison's Principles of Internal Medicine, $12^{th}$ Edition, 1991, Pages 1314–1315). In other words, powdered D,L-threo-hex-2-enono-1,4-lactone stops any bleeding and forms black blood coagulation on contact, with the same amount of powdered D,L-threo-hex-2-enono-1,4-lactone per unit volume of blood for any normal or diseased blood.

The present methods available to stop bleeding in surgery are cautery, epinephrine injection, pressure and some fiber foam. The cautery can cause tissue necrosis in some cases. The epinephrine, pressure and fiber foam can not work for bleeding tendency patients, and fiber foam can cause tissue hematoma, nor can they work for diffuse capillary bleeding and oozing, while powdered D,L-threo-hex-2-enono-1,4-lactone does not cause any tissue necrosis and work particularly well for diffuse capillary bleeding and oozing and any traditionally uncontrollable bleeding tendency patients such as for patients with liver diseases, hemophilia and rectal anal cancer and for postoperative bleeding tendency of the kinds of aforementioned patients. The D,L-threo-hex-2-enono-1,4-lactone can facilitate wound healing also by increasing type 1 procollagen mRNA in the regulation of collagen synthesis.

SUMMARY OF THE INVENTION

The present invention is directed to a method for stopping bleeding, comprising administering powdered D,L-threo-hex-2-enono-1,4-lactone tablets thereof to the wound site in an amount of 0.1568 grams for every milliliter of blood. This powder has a very potent coagulation action to stop bleeding when spraying topically on the bleeding area for any normal or diseased patients. When the powder comes in contact with the blood, the black tar like material is formed, and later becomes solid. The amount of the powder that is needed to react completely with the blood is proportional to the amount of the blood that comes out of the blood vessels. In rats, one capillary, one venous and one femoral artery bleeding were stanched within one second, if sufficient amount of the powder of D,L-threo-hex-2-enono-1,4-lactone was applied. The artery bleeding needs much more this powder of interest. In the test tube conditions, it requires 0.1568 grams of powdered D,L-threo-hex-2-enono-1,4-lactone added to 1 ml of normal or diseased human blood to turn the mixture black and, after 6 minutes, mixture does not move by shaking or pouring. This is the same for normal, colon cancer and hemophilia patients; 1 ml of normal blood needs 0.1568 grams of D,L-threo-hex-2-enono-1,4-lactone powder, 1 ml of colon cancer needs 0.1568 grams of D,L-threo-hex-2-enono-1,4-lactone, 1 ml of hemophilia blood needs 0.1568 grams of D,L-threo-hex-2-enono-1,4-lactone. Sufficient powdered D,L-threo-hex-2-enono-1,4-lactone is particularly useful to stop bleeding in the case of diffuse capillary oozing and mistakenly cut off artery or arteries that can not be found during massive bleeding so as to save the patients's lives therefor. When D,L-threo-hex-2-enono-1,4-lactone is absorbed into the system, it is good for health by making the leucocytes stronger and slowing the aging process etc. However, at the end of operation before closure, the excessive black tar gel like material can be wiped away with Ringer's solution.

DETAILED DESCRIPTION OF THE INVENTION

The present invention is grounded on applicant's discovery that any bleeding, either normal or diseased blood, is stopped on contact, and is formed black blood coagulation, by administration topically of a composition comprising powdered D,L-threo-hex-2-enono-1,4-lactone or its derivative, D,L-threo-hex-2-enono-1,4-lactone-2-R1-5-R2-6-R3, even when contaminated with impurities, and excipients, in an amount of 0.1568 grams for every milliliter of blood.

A composition comprising powdered D,L-threo-hex-2-enono-1,4-lactone or its derivative, D,L-threo-hex-2-enono-1,4-lactone-2-R1-5-R2-6-R3 contains impurities and excipients. D,L-threo-hex-2-enono-1,4-lactone-2-R1-5-R2-6-R3, wherein R1 is organic residue having molecular weight of from 15–700, R2 is hydrogen or hydroxyl, R3 is hydrogen, acyl, optionally substituted phosphono or sulfo, and R3 and hydroxyl or R2 may form acetal residue or ketal residue, and a salt thereof are provided, D,L-threo-hex-2-enono-1,4-lactone derivative, D,L-threo-hex-2-enono-1,4-lactone-2-R1-5-R2-6-R3, wherein R1 is of the formula-CH2-R, wherein R is a C5–22 straight-chain or branched alkyl;

a C1–10 straight-chain or branched-chain alkyl group having one to three substituents selected from the group comprising the step of: (1) C1–6 alkoxyxarbonyl, (2) phenyl or naphthyl optionally substituted with one to three substituents selected from the group comprising the step of C1–5 alkyl, C1–3 alkoxy, halogen, nitro, amino, oxo, hydroxyl and benzyloxy, (3) benzyl or phenethyl optionally substitutd with one to three substituents selected from the group comprising the step of C1–5 alkyl, C1–3 alkoxy, halogen, nitro, amino, oxo, hydroxyl and benzyloxy, (4) phenylcarbonyloxy or naphthylcarbonyloxy optionally substituted with one to three substituents selected from the group comprising the step of C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group comprising the step of: C1–5 alkyl, C1–3 alkoxy, halogen, nitro, amino, oxo, hydroxy and benzyloxy, (6) 2,3,5-trimethyl-1,4-benzoquinonyl, (7) 2,3-dimethoxy- 5-methyl-1,4-benzoquinonyl and (8) 2-methyl-1,4-napthoquinonyl;

a C2–20 alkenyl group having one to three substituents selected from phenyl, naththyl, benzyl or phenethyl, 3-pyridyl, thienyl and furyl;

a phenyl, naphthyl, benzyl or phenethyl optionally substituted with one to three substituents selected from the group comprising the step of C1–5 alkyl, methoxy, methylenedioxy and hydroxyl;

a C1–9 acyl group selected from the group comprising the step of formyl, acetyl, propionyl, n-butyryl, isobutyryl, benzoyl, morpholino-carbonyl, C1–3 alkoxycarbonyl prrolidinocarbonyl, C1–3 alkoxycarbonyl, phenylcarbonyl or naphthylcarbonyl optionally substituted with one to three substitutents selected from the group comprising the step of: hydroxyl, C1–5 alkyl and C1–3 alkoxy, benzylcarbonyl or phenethylcarbonyl optionally substituted with one to three substitutents selected from the group comprising the step of: hydroxyl, C1–5 alkyl and C1–3 alkoxy;

a phenyloxy, naphthyloxy, benzyloxy or phenethyloxy optionally substituted with one to three substitutents selected from the group comprising the step of: hydroxyl, C1–5 alkyl and C1–3 alkoxy;

R2 is hydrogen or hydroxy; and

R3 is hydrogen, or acyl; or R2 and R3 may together form an O,O-isopropylidene residue; or a pharmaceutically acceptable salt thereof, and a pharmaceutically acceptable carier, vehicle or diluent therefor.

The derivative, D,L-threo-hex-2-enono-1,4-lactone-2-R1-5-R2-6-R3, wherein R3 is acyl, R1 is a C1–10 straight chain or branched chain alkyl group which has one to three substituents, the substituent being the class comprising the step of: (1) C1–6 alkoxycarbonyl, (2) phenyl or naphthyl which may hve one or three substituents(s) of the class comprising the step of: C1–5 alkyl, C1–3 alkoxy, halogen, nitro, amino, oxo, hydroxyl and benzyloxy, (3) benzyl or phenethyl which may have one to three substituents(s) of the class comprising the step of: C1–5 alkyl, C1–3 alkoxy, halogen, nitro, amino, oxo, hydroxyl and benzyloxy, (4) phenylcarbonyloxy or naphthylcabonyloxy which may have one to three substituents(s) of the class comprising the step of: C1–5 alkyl, C1–3 alkoxy, halogen, nitro, amino, oxo, hydroxyl and benzyloxy, (5) benzylcarbonyloxy or phenethylcarbonyloxy which may have one to three substituents(s) of the class comprising the step of: C1–5 alkyl, C1–3 alkoxy, halogen, nitro, amino, oxo, hydroxyl and benzyloxy, (6) 2,3,5-trimethyl-1,4-benzoquinonyl, (7) 2,3-dimethoxy-5-methyl-1,4-benzoquinonyl, (7) 2,3-dimethoxy-5-methyl-1,4-benzoquinonyl and (8) 2-methyl-1,4-naphthoquinonyl.

The derivative, D,L-threo-hex-2-enono-1,4-lactone-2-R1-5-R2-6-R3, wherein R1 is a C2–20 alkenyl group which may have one to three substituent(s), the substituent being the class comprising the step of phenyl, naphthyl, benzyl, phenethyl, 3-pyridyl, thienyl and furyl.

The derivative, D,L-threo-hex-2-enono-1,4-lactone-2-R1-5-R2-6-R3, wherein R1 is a phenyl, naphthyl, benzyl, or phenethyl group which may have one to three substituent(s), the substituent being the class comprising the step of C1–5 alkyl, methoxy, methylenedioxy and hydroxyl The derivative, D,L-threo-hex-2-enono-1,4-lactone-2-R1-5-R2-6-R3, wherein R1 is a C1–9 acyl group of the class comprising the step of: formyl, acetyl, propionyl, n-butyryl, isobutyryl, benzoyl, morpholinocarbonyl, C1–3 alkoxycarbonylpyrrolidinocarbonyl , C1–3 alkoxycarbonyl phenylcarbonyl or naphthylcarbonyl which have one to three substituent(s) of the class comprising the step of hydroxyl group, C1–5 alkyl and C13 alkoxy.

The derivative, D,L-threo-hex-2-enono-1,4-lactone-2-R1-5-R2-6-R3, wherein R1 is phenyloxy, naphthyloxy, benzyloxy, or phenethyloxy group which may have one to three substituent(s), the substituent being the class comprising the step of: hydroxyl group, C1–5 alkyl group and C1–3 alkoxy group.

The derivative, D,L-threo-hex-2-enono-1,4-lactone-2-R1-5-R2-6-R3, wherein R1 is —(CH2)10COOCH3, R2 is hydroxyl and R3 is hydrogen.

The derivative, D,L-threo-hex-2-enono-1,4-lactone-2-R1-5-R2-6-R3, wherein R1 is —(CH2)17CH3, R2 is hydroxyl and R3 is nicotynoyl.

A method for stopping bleeding which comprises administering to the bleeding site an effective amount of D,L-threo-hex-2-enono-1,4-lactone-2-R1-5-R2-6-R3, wherein R1 is of the formula —CH2-R, wherein R is C5–22 straight chain or branched alkyl;

a C1–10 straight chain or branched chain alkyl group having one to three substituents selected from the group comprising the step of: (1) C1–6 alkoxycarbonyl, (2) phenyl or naphthyl optionally substituted with one to three substituents selected from the group comprising the step of: C1–5 alkyl, C1–3 alkoxy, halogen, nitro, amino, oxo, hydroxyl and benzyloxy, (3) benzyl or phenethyl optionally substituted with one to three substituents selected from the group comprising the step of C1–5 alkyl, C1–3 alkoxy, halogen, nitro, amino, oxo, hydroxyl and benzyloxy, (4) phenylcarbonyloxy or naphthlcarbonyloxy optionally substituted with one to three substituents selected from the group comprising the step of: C1–5 alkyl, C1–3 alkoxy, halogen, nitro, amino, oxo, hydroxyl and benzyloxy, (5) benzylcarbonyloxy or phenethycarbonyloxy optionally substituted with one to three substituents selected from the group comprising the step of: C1–5 alkyl, C1–3 alkoxy, halogen, nitro, amino, oxo, hydroxyl and benzyloxy, (6) 2,3,5-trimethyl-1,4-benzoquinonyl, (7) 2,3-dimethoxy-5-methyl-1,4-benzoquinoyl and (8) 2-methyl-1,4-napthquinonyl;

a C2–20 alkenyl group having one to three substituents selected from phenyl, naphthyl, benzyl, phenethyl, 3-pyridyl, thienyl and furyl;

a phenyl, napthyl, benzyl or phenethyl optionally substituted with one to three substituents selected from the group comprising the step of: C1–5 alkyl, methoxy, methyleneioxy and hydroxyl;

a C1–9 acyl group selected from the group consisting of formyl, acetyl, propionyl, n-butyryl, isobutyryl, benzoyl, morpholino-carbonyl, C1–3 alkoxycarbonylpyrrolininocarbonyl, C1–3 alkoxycarbonyl, phenylcarbonyl or naphthylcarbonyl optionally substituted with one to three substituents selectd from the group comprising the step of: hydroxyl, C1–5 alkyl and C1–3alkoxy, benzylcarbonyl or phenethylcarbonyl optionally substituted with one to three substituents selected from the group comprising the step: of hydroxyl, C1–5 alkyl and C1–3 alkoxy;

a phenyloxy, naphthloxy, bezyloxy or phenethyloxy optionally substituted with one to three substituents selected from the group comprising the step of hydroxyl, C1–5 alkyl and C1–3 alkoxy;

R2 is hydrogen or hydroxy; and

R3 is hydrogen, or acyl; or R2 and R3 may together form an O,O-isopropylidene Ressdue;

Or pharmaceutically acceptable salt thereof.

The derivative, D,L-threo-hex-2-enono-1,4-lactone-2-R1-5-R2-6-R3, wherein R1 is straight chain or branched alkyl having 1 to 10 carbon atoms optionally substituted with a member selected from a group comprising the step of: hydroxyl, carboxyl, aminocarbonyl, vinyl, ethynyl and quinonylmethyl.

The derivative, D,L-threo-hex-2-enono-1,4-lactone-2-R1-5-R2-6-R3, wherein R straight chain alkyl having 9 to 20 carbon atoms. D,L-threo-hex-2-enono-1,4-lactone R1-5-R2-6-R3, wherein R2 is hydroxyl, R3 is hydrogen. D,L-threo-hex-2-enono-1,4-actone-2-R1-5-R2-6-R3, wherein R3 and hydroxyl or R2 form O,O-isopropylidene residue, R1 is —(CH2)17CH3, R2 is hydroxyl and R3 is hydrogen. While the present composition and method are particularly directed at treatment of bleeding in humans it finds the same application for veterinary use. As the liver is he site of syntheses of all coagulation factors except factor 8, prior to the present invention, nothing has, to the best of my knowledge, been made to stop bleeding on contact, for the massive bleeding tendency patients afflicted with liver diseases, cancer or hemophilia. The treatment for hepatic coagulopathy (coagulation factor disorders associated with liver diseases) and hemophilia is the replacement therapy for transfusion of fresh frozen plasma and factor 8 or 9 concentrates respectively, Lawrence M. Tierney, Jr., et al, Current Medical Diagnosis & Treatment, 1994, $33^{rd}$ Annual Revision, P. 458–459, but that will not stop bleeding on time in a wound caused by trauma or surgery; some patients bled to death simply because of extraction of teeth or tonsilectomy. As soon as a composition comprising powdered D,L-threo-hex-2-enomo-1,4-lactone or its derivative claims with all aforementioned substituents not limiting their scope contact with blood, even in massive bleeding when an artery is cut off, the black gel film like structure forms on the surface of the pond of blood, that stops the fluid of blood moving. If stirring the blood to break through the surface film like structure that keeps the blood fluid from moving when the powder is insufficient, it will bleed again, but much slower than before pouring the powder into the bleeding area; adding sufficient powder into the blood, stirring makes the powder molecules well saturated with the hemoglobin and plasma protein molecules and thus forming the concentrated black sticky gel like structure. In conclusion, D,L-threo-hex-2-enono-1,4-lactone or its derivative claims with all aforementioned substituents not limiting their scope stop bleeding on contact, either in normal or diseased blood.

The invention is further illustrated in the following examples, none of which are to be construed as limiting the invention in any respect.

The following example reports the results of an animal study and a clinical evidence of a composition or the present invention in the treatment of bleeding.

ANIMAL EXPERIMENTS

Example 1

Sufficient composition comprising powdered D,L-threo-hex-2-enono-1,4-lactone and excipients stops massive bleeding of femoral artery on contact when femoral artery of a rat is cut off In this case of artery on contact when femoral artery of a rat is cut off. In this case of artery bleeding, it is administered topically by pouring instead of spraying. Although the amount of the powder needed varies with rats, 0.1344 grams is usually sufficient to stop bleeding within one second for the femoral artery of the rat. The black tar like material is formed in one second as soon as the powder contacts with the blood. Those white spots indicate the powder that is not yet mixed up with the blood. The gel forms first on the surface of the pond of blood, that stops the fluid moving. If stirring the blood to break through the surface film like structure that keeps the blood fluid from moving when the powder is insufficient, it will bleed again, but much slower than before pouring the powder into the bleeding area; adding sufficient powder into the blood, stirring makes the powder molecules well saturated with the hemoglobin and plasma protein molecules and thus forming the concentrated black gel like structure. After 5–6 minutes, when most of the sticky tar like structure is wiped away, it appears there is no bleeding at all.

Example 2

In the case of capillary bleeding in which one capillary is cut off, about 0.0112 grams of this powder stops the bleeding on contact. After 1 minute count from adding the powder, it appears there is no more bleeding at all in a rat.

Example 3

While in the case of one vein cut off in a rat, it needs about 0.0224 grams of the powder to stop bleeding on contact, and about 1½ minutes after the black coagulation is wiped away, it appears there is no more bleeding.

Example 4

The nostril of a rat is cut slightly to bleed, the bleeding stops on contact when applying 0.0037 grams of this powder to the bleeding nostril.

Example 5

After injection of histamin into the rat, it induces secretion of gastric acid, applying the powder topically to the bleeding area, the black coagulation formed, but slower than normal, since the secretion dilutes the black coagulation. Thus this powder can treat the gastric ulcer bleeding when ingested orally.

CLINICAL EVIDENCE

Example 6

Scalp Tumor Excision

Age 32, male, scalp tumor excision, massive bleeding when the tumor is excised. Sufficiently spraying this powder to the bleeding area, the bleeding atops on contact, after the coagulation is washed away, it is closed by suture.

Example 7

A-V Fistula Plasty

Age 40, female, acute renal failure, A-V fistula formation operation, massive bleeding. The operation of stopping bleeding consists of combing the powder with pressing with gauzes. When aedministering this powder to the bleeding area, those that look black in color indicate the black blood coagulation, while those that are white are the powder that does not get mixed up with the blood yet. At the end of the operation, most of black blood coagulation is wiped out with 4×4 gauze, and rinsed with Ringer's solution. It takes totally 5 minutes to stop the bleeding completely, as the surgeon keeps wiping away the coagulation. The patient's conditions are particularly well, better than without using this powder.

Example 8

Skin Contracture Excision

Age 40, male, skin contracture on the palm, which needs to be removed, and it requires skin graft. When the skin graft is removed from the hand, massive bleeding occurs. On applying sufficient powder to the bleeding area topically, it appears black coagulation on contact. Bleeding stops at the same time as the the black coagulation forms. Those that appears more black area indicate the more powder mixed up with the blood. Suture going on.

Example 9

Paraanal Abscess Excision

Age 70, female, paraanal excision, bleeding when it is opened up. When spraying the powder to the bleeding area, it stops bleeding by forming black blood coagulation on contact. Those that appears white are the powder that are not mixed up with the blood. Suture going on.

Example 10

Paraanal Abscess Excision

Age 50, male, paranal abscess Excision, massive bleeding when it is opened. On spraying the powder topically to the bleeeding area, the black color is formed on contact because of the blood coagulation. The white color is the powder instantly not mixed up with the blood yet. Lastly, insert the long gauze into the anus.

Example 11

Extraction of Tooth

Age 30, male, extraction of tooth, gum injected bleeds, Administering this powder topuically to the bleeding area, the bleeding stops on contact and black blood coagulation forms at the same time. Wipe out the black coagulation in 10 seconds, stopped bleeding still persisted.

Example 12

Extraction of Teeth for Chronic Hepatitis

Age 60, female, chronic hepatitis, has bleeding tendency, extraction of teeth causes massive bleeding. Upon applying this powder to the socket of the gum, the black coagulation forms on contact, and the bleeding in the socket stops on contact accordingly.

Example 13

Finger Scratched

Myself, finger little scratched, slightly bleeds. Upon contact with the powder, the black color forms on contact.

Example 14

Normal, liver Disease, Colon Cancer and Hemophilia Blood When tested in the tube, 1 milliliter of human blood requires 0.1568 grams of a composition comprising powdered D,L-threo-hex-2-enono-1,4-lactone to form black blood coagulation by shaking the tube with hand or stirrer machine. It takes 6 minutes to cause the black blood coagulation unmobile in the test tube for normal, liver diseases, colon cancer and hemophilia blood respectively. These experiments have indicated that the mechanism of action of powdered D,L-threo-hex-2-enono-1,4-lactone in the formation of black blood coagulation does not involve the coagulation factors.

Example 15

My Finger Scratched to Bleed

My finger scratched to bleed, for example, when the derivative, D,L-threo-hex-enono-1,4-lactone-2-phosphate, D,L-threo-hex-2-enono-1,4-lactone-6-palimitate, D,L-threo-hex-2-enono-1,4-lactone-2-benzoate, D,L-threo-hex-2-enono-1,4-lactone-2-propane in powder or gel or liquid form was applied to the bleeding site, the black blood coagulation was formed and bleeding was stopped on contact.

I claim:

1. A method for stopping bleeding at a bleeding site of a human or an animal in body tissue caused by pathological changes, trauma or surgery, comprising administering topically to the bleeding site powdered D,L-threo-hex-2-enono-1,4-lactone and excipients.

2. The method of claim 1 wherein powdered ascorbic acid, impurities, and excipients are in a liquid form.

3. The method of claim 1 wherein powdered ascorbic acid, impurities, and excipients are in a tablet form.

4. The method of claim 1 wherein the compound is sodium D,L-threo-hex-2-enono-1,4-lactone.

5. The method of claim 1 wherein D,L-threo-hex-2-enono-1,4-lactone is a derivative, D,L-threo-hex-2-enono-1,4-lactone-2-R1-5-R2-6-R3, wherein R1 is organic residue having molecular weight of from 15 to 700 or R2 is hydrogen or hydroxyl, R3 is hydrogen, acyl, optionally substituted phosphono or sulfo, and R3, and hydoxyl or R2 may form acetal residue or ketal residue, and a salt thereof provided, wherein R1 is of the formula-CH2-R, wherein R is C5–22 straight-chain or branched alkyl;

a C1–10 straight-chain or branched-chain alkyl group having one to three substituents selected from the group consisting of: (1) C1–6 alkoxycarbonyl, (2) phenyl or naphthyl optionally substituted with one to three substituents selected from the group consisting of C1–5 alkyl, C1–3 alkoxy, halogen, nitro, amino, oxo, hydroxyl and benzyloxy, (3) benzyl or phenethyl optionally substituted with one to three substituents selected from the group consisting of: C1–5 alkyl, C1–3 alkoxy, halogen, nitro, amino, oxo, hydroxyl and benzyloxy, (4) phenylcarbonyloxy or naphthylcarbonloxy optionally substituted with one to three substituents selected from the group consisting of: C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group consisting of: C1–5 alkyl, C1–3 alkoxy, halogen, nitro, amino, oxo, hydroxy and bezyloxy, (6) 2,3,5-trimethyl-1,4-benzoquinonyl, (7) 2,3-dimethoxy-5-methyl-1,4-benzoquinonyl and (8) 2-methyl-1,4-napthoquinonyl;

a C2–20 alkenyl group having one to three substituents selected from the group consisting of benzyl or phenethyl, 3-pyridyl, thienyl and furyl;

a phenyl, naphthyl, benzyl or phenethyl optionally substituted with one to three substituents selected from the group consisting of: C1–5 alkyl, methoxy, methylenedioxy and hydroxyl;

a C1–9 acyl group selected from the group consisting of: formyl, acetyl, propionyl, n-butyryl isobutyryl, benzoyl, morpholino-carbonyl, C1–3 alkoxycarbonyl prrolidinocarbonyl, C1–3 alkoxycarbonyl, phenylcarbonyl or naphthylcarbonyl optionally substituted with one to three substituents selected from the group consisting of; hydroxyl, C1–5 alkyl and C1–3 alkoxy, benzylcarbonyl or phenethylcarbonyl optiopnally substituted with one to three substituents selected from the group consisting of: hydroxyl, C1–5 alkyl and C1–3 alkoxy, a phenyloxy, naphthloxy, benzyloxy or phenethyloxy optionally substituted with one to three substituents selected from the group consisting of: hydroxyl, C1–5 alkyl and C1–3 alkoxy,R2 is hydrogen or hydroxy; and R3 is hydrogen, or acyl; or R2 and R3 may form an O,O-isopropylidene residue; or a pharmaceutically acceptable salt thereof, and a pharmaceutically acceptable carrier, vehicle or diluent therefor.

6. A method of stopping bleeding which comprises administering an effective amount of D,L-threo-hex-2-enono-1,4-lactone derivative, D,L-threo-hex-2-enono-1,4-lactone-2-R1-5-R2-R3, wherein R1 is of the formula —CH2—R wherein R is a C5–22 straight-chain or branched alkyl; a C1–10 straight-chain or branched-chain alkyl group having 1 to 3 substituents selected from the group consisting of: (1) C1–6 alkoxycarbonyl, (2) phenyl or naphthyl optionally substituted with one to three substituents selected from the group consisting of C1–5 alkyl, C1–3 alkoxy, halogen, nitro, amino, oxo, hydroxyl and benzyloxy, (3) benzyl or phenethyl optionally substituted with one to three substituents selected from the group consisting of: C1–5 alkyl, C1–3 alkoxy, halogen, nitro, amino, oxo, hydroxyl and benzyloxy, (4) phenylcarbonyloxy or naphthylcarbonyloxy optionally substituted with one to three substituents selected from the group consisting of C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group consisting of: C1–5 alkyl, C1–3 alkoxy, halogen, nitro, amino, oxo, hydroxy and benzyloxy, (6) 2,3,5-trimethyl-1,4-benzoquinonyl, (7)2,3-dimethoxy-5-methyl-1,4-benzoquinonyl and (8) 2-methyl-1,4-napthoquinonyl;

a C2–20 alkenyl group having one to three substituents selected from the group consisting of phenyl, naththyl, benzyl or phenethyl, 3-pyridyl, thienyl and furyl;

a phenyl, naphthyl, benzyl, phenethyl optionally substituted with one to three substituents selected from the group consisting of: C–5 alkyl, methoxy, methylenedioxy and hydroxyl;

a C1–9 acyl group selected from the group consisting of: formyl, acetyl, propionyl, n-butyryl, isobutyryl, benzoyl, morpholino-carbonyl, C1–3 alkoxycarbonyl prrolidinocarbonyl, 1–3 alkoxycarbonyl, phenylcarbonyl or naphthylcarbonyl optionally substituted with one to three substituents selected from the group consisting of: hydroxyl, C1–5 alkyl and C1–3 alkoxy, benzylcarbonyl or phenethylcarbonyl optionally substituted with one to three substituents selected from the group consisting of: hydroxyl, C1–5 alkyl and C1–3 alkoxy; benzylcarbonyl or phenethycarbonyl optionally substituted with one to three substituents selected from the group consisting of: hydroxyl, C1–5 alkyl and C1–3 alkoxy;

a phenyloxy, naphthyloxy, benzyloxy or phenethyloxy optionally substituted with one to three substituents selected from the group consisting of: hydroxyl, C1–5 alkyl and C1–3 alkoxy;

R2 is hydrogen or hydroxy, and R3 is hydogen, or acyl; or R2 and R3 may together form an O,O-isopropylidene residue; or pharmaceutically acceptable salt thereof, and a pharmaceutically acceptable carrier, vehicle or diluent therefor; wherein R3 is acyl.

7. The method according to claim 5, wherein R1 is a C1–10 straight chain or branched chain alkyl group which has one to three substituents, the substituent being selected from the group consisting of: (1) C1–6 alkoxycarbonyl, (2) phenyl or naphthyl which may have one or three substituent(s) selected from the group consisting of: C1–5 alkyl, C1–3 alkoxy, halogen, nitro, amino, oxo, hydroxyl and benzyloxy, (3) benzyl or phenethyl which may have one to three substituent(s) selected from the group consisting of: C1–5 alkyl, C1–3 alkoxy, halogen, nitro, amino, oxo, hydroxyl and benzyloxy, (4) phenylcarbonyloxy or naphthylcarbonyloxy which may have one to three substituents selected from the group consisting of C1–5 alkyl, C1–3 alkoxy, halogen, nitro, amino, oxo, hydroxyl and benzyloxy, (5) benzylcarbonyloxy or phenethylcarbonyloxy which may have one to three substituent(s) selected from the group consisting of C1–5 alkyl, C1–3 alkyl, C1–3 alkoxy, halogen, nitro, amino, oxo, hydroxyl and benzyloxy, (6) 2,3,5-trimethyl-1,4-benzoquinonyl, (7) 2,3-dimethoxy-5-methyl-1,4-benzoquinonyl, (7) 2,3-dimethoxy-5-methyl-1,4-benzoquinonyl and (8) 2-methyl-1,4-naphthoquinonyl.

8. The method according to claim 5 wherein R1 is a C2–20 alkenyl group which may have one to three substituent(s), the substituent being selected from the group consisting of: phenyl, naphthyl, benzyl, phenethyl, 3-pyridyl, thienyl and furyl.

9. The method according to claim 5, wherein R1 is a phenyl, naphthyl, benzyl, or phenethyl group which may have one to three substituent(s), the substituent being selected from the group consisting of: C1–5 alkyl, methoxy, methylenedioxy and hydroxyl.

10. The method according to claim 5, wherein R1 is a C1–9 acyl group selected from the group consisting of: formyl, acetyl, propionyl, n-butyryl, isobutyryl, benzoyl, morpholinocarbonyl, C1–3 alkoxycarbonylpyrrolidinocarbonyl, C1–3 alkoxycarbonyl phenylcarbonyl or naphthylcarbonyl which have one to three substituent(s) selected from the group consisting of: hydroxyl group, C1–5 alkyl and C1–3 alkoxy.

11. The method according to the claim 5, wherein R1 is phenyloxy, naphthyloxy, benzyloxy, or phenenethyloxy group which may have one to three substituent(s), the substituent being selected from the group consisting of: C1–5 alkyl group and C1–3 alkoxy group.

12. A method of stopping bleeding which comprises administering an effective amount of D,L-threo-hex-2-enono-1,4-lactone derivative, D,L-threo-hex-2-enono-1,4-lactone-2-R1-5-R2-6-R3 wherein R1 is of the formula —CH2—R, wherein R is a C5–22 straight-chain or branched alkyl; a C1–10 straight-chain or branched-chain alky group having one to three substituents selected from the group consisting of: (1) C1–6 alkoxycarbonyl, (2) phenyl or naphthyl optionally substituted with one to three substituents selected from the group consisting of C1–5 alkyl, C1–3 alkoxy, halogen, nitro, amino, oxo, hydroxyl and benzyloxy, (3) benzyl or phenethyl optionally substituted with one to three substituents selected from the group consisting of: C1–5 alkyl, C1–3 alkoxy, halogen, nitro, amino, oxo, hydroxyl and benzyloxy, (4) phenylcarbonyloxy or naphthycarbonyloxy optionally substituted with one to three substituents selected from the group consisting of C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group consisting of: C1–5 alkyl, C1–3 alkoxy, halogen, nitro, amino, oxo, hydroxy and benzyloxy, (6) 2,3,5-trimethyl-1,4-benzoquinonyl, (7)2,3-dimethoxy-5-methyl-1,4-benzoquinonyl and (8) 2-methyl-1,4-napthoquinonyl;

a C2–20 alkenyl group having one to three substituents selected from the group consisting of phenyl, naththyl, benzyl or phenethyl, 3-pyridyl, thienyl and furyl;

a phenyl, naphthyl, benzyl, phenethyl optionally substituted with one to three substituents selected from the group consisting of: C1–5 alkyl, methoxy, methylenedioxy and hydroxyl;

a C1–9 acyl group selected from the group consisting of: formyl, acetyl, propionyl, n-butyryl, isobutyryl, benzoyl, morpholino-carbonyl, C1–3 alkoxycarbonyl prrolidinocarbonyl, 1–3 alkoxycarbonyl, phenylcarbonyl or naphthylcarbonyl optionally substituted with one to three substituents selected from the group consisting of hydroxyl, C1–5 alkyl and C1–3 alkoxy, benzylcarbonyl or phenethylcarbonyl optionally substituted with one to three substituents selected from the group consisting of: hydroxyl, C1–5 alkyl and C1–3 alkoxy; benzylcarbonyl or phenethycarbonyl optionally substituted with one to three substituents selected from the group consisting of hydroxyl, C1–5 alkyl and C1–3 alkoxy;

a phenyloxy, naphthyloxy, benzyloxy or phenethyloxy optionally substituted with one to three substituents selected from the group consisting of hydroxyl, C1–5 alkyl and C1–3 alkoxy;

R2 is hydrogen or hydroxy; and R3 is hydogen, or acyl; or R2 and R3 may together form an O,O-isopropylidene residue, or pharmaceutically acceptable salt thereof, and a pharmaceutically acceptable carrier, vehicle or diluent therefor; wherein, R1 is —(CH2)10COOCH3, R2 is hydroxyl and R3 is hydrogen.

13. A method of stopping bleeding which comprises administering to the bleeding site an effective amount of D,L-threo-hex-2-enono-1,4-lactone derivative, D,L-threo-hex-2-enono-1,4-lactone-2-R1-5-R2-6-R3 to stop bleeding on contact, wherein R1 is of the formula —CH2—R, wherein R is a C5–22 straight-chain or branched alkyl; a C1–10 straight-chain or branched-chain alky group having one to three substituents selected from the group consisting of: (1) C1–6 alkoxycarbonyl, (2) phenyl or naphthyl optionally substituted with one to three substituents selected from the group consisting of C1–5 alkyl, C1–3 alkoxy, halogen, nitro, amino, oxo, hydroxyl and benzyloxy, (3) benzyl or phenethyl optionally substituted with one to three substituents selected from the group consisting of: C1–5 alkyl, C1–3 alkoxy, halogen, nitro, amino, oxo, hydroxyl and benzyloxy, (4) phenylcarbonyloxy or naphthycarbonyloxy optionally substituted with one to three substituents selected from the group consisting of C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group consisting of: C1–5 alkyl, C1–3 alkoxy, halogen, nitro, amino, oxo, hydroxy and benzyloxy, (6) 2,3,5-trimethyl-1,4-benzoquinonyl, (7)2,3-dimethoxy-5-methyl-1,4-benzoquinonyl and (8) 2-methyl-1,4-napthoquinonyl;

a C2–20 alkenyl group having one to three substituents selected from the group consisting of phenyl, naththyl, benzyl or phenethyl, 3-pyridyl, thienyl and furyl;

phenyl, naphthyl, benzyl, phenethyl optionally substituted with one to three substituents selected from the group consisting of: C1–5 alkyl, methoxy, methylenedioxy and hydroxyl;

a C1–9 acyl group selected from the group consisting of: formyl, acetyl, propionyl, n-butyryl, isobutyryl, benzoyl, morpholino-carbonyl, C1–3 alkoxycarbonyl prrolidinocarbonyl, 1–3 alkoxycarbonyl, phenylcarbonyl or naphthylcarbonyl optionally substituted with one to three substituents selected from the group consisting of: hydroxyl, C1–5 alkyl and C1–3 alkoxy, benzylcarbonyl or phenethylcarbonyl optionally substituted with one to three substituents selected from the group consisting of: hydroxyl, C1–5 alkyl and C1–3 alkoxy; benzylcarbonyl or phenethycarbonyl optionally substituted with one to three substituents selected from the group consisting of hydroxyl, C1–5 alkyl and C1–3 alkoxy;

a phenyloxy, naphthyloxy, benzyloxy or phenethyloxy optionally substituted with one to three substituents selected from the group consisting of hydroxyl, C1–5 alkyl and C1–3 alkoxy;

R2 is hydrogen or hydroxy; and R3 is hydogen, or acyl; or R2 and R3 may together form an O,O-isopropylidene residue; or pharmaceutically acceptable salt thereof, and a pharmaceutically acceptable carrier, vehicle or diluent therefor; wherein R1 is —(CH2)17CH3, R2 is hydroxyl and R3 is nicotynoyl.

14. A method of stopping bleeding which comprises administering to the bleeding site an effective amount of D,L-threo-hex-2-enono-1,4-lactone-2-R1-5-R2-6-R3, wherein R1 is of the formula —CH2—R, wherein R is C5–22 straight chain or branched alkyl;

a C1–10 straight chain or branched chain alkyl group having one to three substituents selected from the group consisting of: (1) C1–6 alkoxycarbonyl, (2) phenyl or naphthyl optionally substituted with one to three substituents selected from the group consisting of C1–5 alkyl, C1–3 alkoxy, halogen, nitro, amino, oxo, hydroxyl and benzyloxy, (3) benzyl or phenethyl optionally substituted with one to three substituents selected from the group consisting of: $C_{1-5}$ alkyl, C1–3 alkoxy, halogen, nitro, amino, oxo, hydroxyl and benzyloxy, (4) phenylcarbonyloxy or naphthcarbonyloxy optionally substituted with one to three substituents selected from the group consisting of: C1–5 alkyl, C1–3 alkoxy, halogen, nitro, amino, oxo, hydroxyl and benzyloxy, (5) benzylcarbonyloxy or phenethycarbonyloxy optionally substituted with one to three substituents selected from the group consisting of: C1–5 alkyl, C1–3 alkoxy, halogen, nitro, amino, oxo, hydroxyl and benzyloxy, (6) 2,3,5-trimethyl-1,4-benzoquinonyl, (7) 2,3-dimethoxy-5-methyl-1,4-benzoquinoyl and (8) 2-methyl-1,4-naphthquinonyl;

a C2–20 alkenyl group having one to three substituents selected from phenyl, naphthyl, benzyl, phenethyl, 3-pyridyl, thienyl and furyl;

a phenyl, napthyl, benzyl or phenethyl optionally substituted with one to three substituents selected from the group consisting of: C1–5 alkyl, methoxy, methyleneioxy and hydroxyl;

a C1–9 acyl group selected from the group consisting of formyl, acetyl propionyl, n-butyry, isobutyryl, benzoyl, morpholino-carbonyl, C1–3 alkoxycarbonylpyrrolininocarbonyl, C1–3 alkoxycarbonyl, phenylcarbonyl or naphthylcarbonyl optionally substituted with one to three substituents selected from the group consisting of: hydroxyl C1–5 alkyl and C1–3 alkoxy, benzylcarbonyl or phenethylcarbonyl optionally substituted with one to three substituents selected from the group consisting of: hydroxyl, C1–5 alkyl and C1–3 alkoxy;

a phenyloxy, naphthloxy, benzyloxy or phenethyloxy optionally substituted wih one to thre substituents selected from the group consisting of: hydroxyl, C1–5 alkyl and C1–3 alkoxy;

R2 is hydrogen or hydroxy; and

R3 is hydrogen, or acyl; or R2 and R3 may together form an O,O-isopropylidene residue;

or pharmaceutically acceptable salt thereof.

15. The method of claim 11, wherein R1 is straight chain or branched alkyl having 1 to 10 carbon atoms optionally substituted with a member selected from a group consisting of: hydroxyl, carboxyl, aminocarbonyl, vinyl, ethynyl and quinonylmethyl.

16. A method of stopping bleeding which comprises administering an effective amount of D,L-threo-hex-2-enono-1,4-lactone derivative, D,L-threo-hex-2-enono-1,4-lactone-2-R1-5-R2-6-R3, wherein R1 is of the formula —CH2—R, wherein R is a C5–22 straight-chain or branched alkyl; a C1–10 straight-chain or branched-chain alky group having one to three substituents selected from the group consisting of: (1) C1–6 alkoxycarbonyl, (2) phenyl or naphthyl optionally substituted with one to three substituents selected from the group consisting of C1–5 alkyl, C1–3 alkoxy, halogen, nitro, amino, oxo, hydroxyl and benzyloxy, (3) benzyl or phenethyl optionally substituted with one to three substituents selected from the group consisting of: C1–5 alkyl, C1–3 alkoxy, halogen, nitro, amino, oxo, hydroxyl and benzyloxy, (4) phenylcarbonyloxy or naphthycarbonyloxy optionally substituted with one to three substituents selected from the group consisting of C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group consisting of: C1–5 alkyl, C1–3 alkoxy, halogen, nitro, amino, oxo, hydroxy and benzyloxy, (6) 2,3,5-trimethyl-1,4-benzoquinonyl, (7)2,3-dimethoxy-5-methyl-1,4-benzoquinonyl and (8) 2-methyl-1,4-napthoquinonyl;

a C2–20 alkenyl group having one to three substituents selected from the group consisting of phenyl, naththyl, benzyl or phenethyl, 3-pyridyl, thienyl and furyl;

a phenyl, naphthyl, benzyl, phenethyl optionally substituted with one to three substituents selected from the group consisting of: C1–5 alkyl, methoxy, methylenedioxy and hydroxyl;

a C1–9 acyl group selected from the group consisting of: formyl, acetyl, propionyl, n-butyryl, isobutyryl, benzoyl, morpholinocarbonyl, C1–3 alkoxycarbonyl prrolidinocarbonyl, 1–3 alkoxycarbonyl, phenylcarbonyl or naphthylcarbonyl optionally substituted with one to three substituents selected from the group consisting of: hydroxyl, C1–5 alkyl and C1–3 alkoxy, benzylcarbonyl or phenethylcarbonyl optionally substituted with one to three substituents selected from the group consisting of: hydroxyl, C1–5 alkyl and C1–3 alkoxy; benzylcarbonyl or phenethycarbonyl optionally substituted with one to three substituents selected from the group consisting of: hydroxyl, C1–5 alkyl and C1–3 alkoxy;

a phenyloxy, naphthyloxy, benzyloxy or phenethyloxy optionally substituted with one to three substituents selected from the group consisting of: hydroxyl, C1–5 alkyl and C1–3 alkoxy;

R2 is hydrogen or hydroxy; and R3 is hydogen, or acyl; or R2 and R3 may together form an O,O-isopropylidene residue; or pharmaceutically acceptable salt thereof, and a pharmaceutically acceptable carrier, vehicle or diluent therefor, wherein R1 is phenyloxy, naphthyloxy, benzyloxy, or phenethyloxy group which may have one to three substituent(s), the substituent being selected from the group consisting of: hydroxyl group, C1–5 alkyl group and C1–3 alkoxy group; wherein R1 is straight chain alkyl having 9 to 20 carbon atoms.

17. A method of stopping bleeding which comprises administering to the bleeding site an effective amount of D,L-threo-hex-2-enono-1,4-lactone derivative, D,L-threo-hex-2-enono-1,4-lactone-2-R1-5-R2-6-R3, wherein R1 is of the formula —CH2—R, wherein R is a C5–22 straight-chain or branched alkyl;

a C1–10 straight-chain or branched-chain alky group having one to three substituents selected from the group consisting of: (1) C1–6 alkoxycarbonyl, (2) phenyl or naphthyl optionally substituted with one to three substituents selected from the group consisting of C1–5 alkyl, C1–3 alkoxy, halogen, nitro, amino, oxo, hydroxyl and benzyloxy, (3) benzyl or phenethyl optionally substituted with one to three substituents selected from the group consisting of: C1–5 alkyl, C1–3 alkoxy, halogen, nitro, amino, oxo, hydroxyl and benzyloxy, (4) phenylcarbonyloxy or naphthycarbonyloxy optionally substituted with one to three substituents selected from the group consisting of C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group consisting of: C1–5 alkyl, C1–3 alkoxy, halogen, nitro, amino, oxo, hydroxy and benzyloxy, (6) 2,3,5-trimethyl-1,4-benzoquinonyl, (7)2,3-dimethoxy-5-methyl-1,4-benzoquinonyl and (8) 2-methyl-1,4-napthoquinonyl;

a C2–20 alkenyl group having one to three substituents selected from the group consisting of phenyl, naththyl, benzyl or phenethyl, 3-pyridyl, thienyl and furyl;

a phenyl, naphthyl, benzyl, phenethyl optionally substituted with one to three substituents selected from the group consisting of: C1–5 alkyl, methoxy, methylenedioxy and hydroxyl;

a C1–9 acyl group selected from the group consisting of: formyl, acetyl, propionyl, n-butyryl, isobutyryl, benzoyl, morpholino-carbonyl, C1–3 alkoxycarbonyl prrolidinocarbonyl, 1–3 alkoxycarbonyl, phenylcarbonyl or napbthylcarbonyl optionally substituted with one to three substituents selected from the group consisting of hydroxyl, C1–5 alkyl and C1–3 alkoxy, benzylcarbonyl or phenethylcarbonyl optionally substituted with one to three substituents selected from the group consisting of: hydroxyl, C1–5 alkyl and C1–3 alkoxy; benzylcarbonyl or phenethycarbonyl optionally substituted with one to three substituents selected from the group consisting of: hydroxyl, C1–5 alkyl and C1–3 alkoxy;

a phenyloxy, naphthyloxy, benzyloxy or phenethyloxy optionally substituted with one to three substituents selected from the group consisting of: hydroxyl, C1–5 alkyl and C1–3 alkoxy;

R2 is hydrogen or hydroxy; and R3 is hydogen, or acyl; or R2 and R3 may together form an O,O-isopropylidene residue, or pharmaceutically acceptable salt thereof, and a pharmaceutically acceptable carrier, vehicle or diluent therefor; wherein R1 is phenyloxy, naphthyloxy, benzyloxy, or phenenethyloxy group which may have one to three-substituent(s), the substituent being selected from the group consisting of: C1–5 alkyl group and C1–3 alkoxy group wherein R2 is hydroxyl.

18. A method of stopping bleeding which comprises administering to the bleeding site an effective amount of D,L-threo-hex-2-enono-1,4-lactone derivative, D,L-threo-hex-2-enono-1,4-lactone-2-R1-5-R2-6-R3, wherein R1 is of the formula —CH2—R, wherein R is a C5–22 straight-chain or branched alkyl; a C1–10 straight-chain or branched-chain alky group having one to three substituents selected from the group consisting of: (1) C1–6 alkoxycarbonyl, (2) phenyl or naphthyl optionally substituted with one to three substituents selected from the group consisting of C1–5 alkyl, C1–3 alkoxy, halogen, nitro, amino, oxo, hydroxyl and benzyloxy, (3) benzyl or phenethyl optionally substituted with one to three substituents selected from the group consisting of: C1–5 alkyl, C1–3 alkoxy, halogen, nitro, amino, oxo, hydroxyl and benzyloxy, (4) phenylcarbonyloxy or naphthycarbonyloxy optionally substituted with one to three substituents selected from the group consisting of C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group consisting of: C1–5 alkyl, C1–3 alkoxy, halogen, nitro, amino, oxo, hydroxy and benzyloxy, (6) 2,3,5-trimethyl-1,4-benzoquinonyl, (7)2,3-dimethoxy-5-methyl-1,4-benzoquinonyl and (8) 2-methyl-1,4-napthoquinonyl;

a C2–20 alkenyl group having one to three substituents selected from the group consisting of phenyl, naththyl, benzyl or phenethyl, 3-pyridyl, thienyl and furyl;

a phenyl, naphthyl, benzyl, phenethyl optionally substituted with one to three substituents selected from the group consisting of: C1–5 alkyl, methoxy, methylenedioxy and hydroxyl;

a C1–9 acyl group selected from the group consisting of: formyl, acetyl, propionyl, n-butyryl, isobutyryl, benzoyl, morpholino-carbonyl, C1–3 alkoxycarbonyl prrolidinocarbonyl, 1–3 alkoxycarbonyl, phenylcarbonyl or naphthylcarbonyl optionally substituted with one to three substituents selected from the group consisting of: hydroxyl, C1–5 alkyl and C1–3 alkoxy, benzylcarbonyl or phenethylcarbonyl optionally substituted with one to three substituents selected from the group consisting of: hydroxyl, C1–5 alkyl and C1–3 alkoxy; benzylcarbonyl or phenethycarbonyl optionally substituted with one to three substituents selected from the group consisting of: hydroxyl, C1–5 alkyl and C1–3 alkoxy;

a phenyloxy, naphthyloxy, benzyloxy or phenethyloxy optionally substituted with one to three substituents selected from the group consisting of: hydroxyl, C1–5 alkyl and C1–3 alkoxy;

R2 is hydrogen or hydroxy; and R3 is hydogen, or acyl; or R2 and R3 may together form an O,O-isopropylidene residue; or pharmaceutically acceptable salt thereof, and a pharmaceutically acceptable carrier, vehicle or diluent therefor; wherein R1 is phenyloxy, naphthyloxy, benzyloxy, or phenenethyloxy group which may have one to three substituent(s), the substituent being selected from the group consisting of: C1–5 alkyl group and C1–3 alkoxy group; wherein R3 is hydrogen.

19. A method of stopping bleeding which comprises administering to the bleeding site an effective amount of D,L-threo-hex-2-enono-1,4-lactone derivative, D,L-threo-hex-2-enono-1,4-lactone-2-R1-5-R2-R3, wherein R1 is of the formula —CH2—R, wherein R is a C5–22 straight-chain or branched alkyl; a C1–10 straight-chain or branched-chain alky group having one to three substituents selected from the group consisting of: (1) C1–6 alkoxycarbonyl, (2) phenyl or naphthyl optionally substituted with one to three substituents selected from the group consisting of C1–5 alkyl, C1–3 alkoxy, halogen, nitro, amino, oxo, hydroxyl and benzyloxy, (3) benzyl or phenethyl optionally substituted with one to three substituents selected from the group consisting of: C–5 alkyl, C1–3 alkoxy, halogen, nitro, amino, oxo, hydroxyl and benzyloxy, (4) phenylcarbonyloxy or naphthycarbonyloxy optionally substituted with one to three substituents selected from the group consisting of C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group consisting of: C1–5 alkyl, C1–3 alkoxy, halogen, nitro, amino, oxo, hydroxy and benzyloxy, (6) 2,3,5-trimethyl-1,4-benzoquinonyl, (7)2,3-dimethoxy-5-methyl-1,4-benzoquinonyl and (8) 2-methyl-1,4-napthoquinonyl;

a C2–20 alkenyl group having one to three substituents selected from the group consisting of phenyl, naththyl, benzyl or phenethyl, 3-pyridyl, thienyl and furyl;

a phenyl, naphthyl, benzyl, phenethyl optionally substituted with one to three substituents selected from the group consisting of: C1–5 alkyl, methoxy, methylenedioxy and hydroxyl;

a C1–9 acyl group selected from the group consisting of: formyl, acetyl, propionyl, n-butyryl, isobutyryl, benzoyl, morpholino-carbonyl, C1–3 alkoxycarbonyl prrolidinocarbonyl, 1–3 alkoxycarbonyl, phenylcarbonyl or naphthylcarbonyl optionally substituted with one to three substituents selected from the group consisting of: hydroxyl, C1–5 alkyl and C1–3 alkoxy, benzylcarbonyl or phenethylcarbonyl optionally substituted with one to three substituents selected from the group consisting of: hydroxyl, C1–5 alkyl and C1–3 alkoxy; benzylcarbonyl or phenethycarbonyl optionally substituted with one to three substituents selected from the group consisting of: hydroxyl, C1–5 alkyl and C1–3 alkoxy;

a phenyloxy, naphthyloxy, benzyloxy or phenethyloxy optionally substituted with one to three substituents selected from the group consisting of: hydroxyl, C1–5 alkyl and C1–3 alkoxy;

R2 is hydrogen or hydroxy; and R3 is hydogen, or acyl; or R2 and R3 may together form an O,O-isopropylidene residue; or pharmaceutically acceptable salt thereof, and a pharmaceutically acceptable carrier, vehicle or diluent therefor; wherein R1 is phenyloxy, naphthyloxy, benzyloxy, or phenenethyloxy group which may have one to three substituent(s), the substituent being selected from the group consisting of: C1–5 alkyl group and C1–3 alkoxy group, wherein R3 and hydroxyl or R2 form O,O-isopropylidene residue.

20. A method of stopping bleeding which comprises administering to the bleeding site an effective amount of D,L-threo-hex-2-enono-1,4-lactone derivative, D,L-threo-hex-2-enono-1,4-lactone-2-R1-5-R2-R3, wherein R1 is of the formula —CH2—R, wherein R is a C5–22 straight-chain or branched alkyl; a C1–10 straight-chain or branched-chain alkyl group having one to three substituents selected from the group consisting of: (1) C1–6 alkoxycarbonyl, (2) phenyl or naphthyl optionally substituted with one to three substituents selected from the group consisting of C1–5 alkyl; C1–3 alkoxy, halogen, nitro, amino, oxo, hydroxyl and benzyloxy, (3) benzyl or phenethyl optionally substituted with one to three substituents selected from the group consisting of: C1–5 alkyl, C1–3 alkoxy, halogen, nitro, amino, oxo, hydroxyl and benzyloxy, (4) phenylcarbonyloxy or naphthycarbonyloxy optionally substituted with one to three substituents selected from the group consisting of C1–5 alkyl, C1–3 alkoxy, halogen, nitro, amino, oxo, hydroxyl and benzyloxy, (5) benzylcarbonyloxy or phenethylcarbonyloxy optionally substituted with one to three substituents selected from the group consisting of: C1–5 alkyl, C1–3 alkoxy, halogen, nitro, amino, oxo, hydroxy and benzyloxy, (6) 2,3,5-trimethyl-1,4-benzoquinonyl, (7) 2,3-dimethoxy-5-methyl-1,4-benzoquinonyl and (8) 2-methyl-1,4-napthoquinonyl;

- a C2–20 alkenyl group having one to three substituents selected from the group consisting of phenyl, naththyl, benzyl or phenethyl, 3-pyridyl, thienyl and furyl;
- a phenyl, naphthyl, benzyl, phenethyl optionally substituted with one to three substituents selected from the group consisting of: C1–5 alkyl, methoxy, methylenedioxy and hydroxyl;
- a C1–9 acyl group selected from the group consisting of: formyl, acetyl, propionyl, n-butyryl, isobutyryl, benzoyl, morpholino-carbonyl, C1–3 alkoxycarbonyl prrolidinocarbonyl, 1–3 alkoxycarbonyl, phenylcarbonyl or naphthylcarbonyl optionally substituted with one to three substituents selected from the group consisting of hydroxyl, C1–5 alkyl and C1–3 alkoxy, benzylcarbonyl or phenethylcarbonyl optionally substituted with one to three substituents selected from the group consisting of: hydroxyl, C1–5 alkyl and C1–3 alkoxy; benzylcarbonyl or phenethycarbonyl optionally substituted with one to three substituents selected from the group consisting of: hydroxyl, C1–5 alkyl and C1–3 alkoxy;
- a phenyloxy, naphthyloxy, benzyloxy or phenethyloxy optionally substituted with one to three substituents selected from the group consisting of: hydroxyl, C1–5 alkyl and C1–3 alkoxy;

R2 is hydrogen or hydroxy; and R3 is hydogen, or acyl; or R2 and R3 may together form an O,O-isopropylidene residue; or pharmaceutically acceptable salt thereof, and a pharmaceutically acceptable carrier, vehicle or diluent therefor; wherein R1 is phenyloxy, naphthyloxy, benzyloxy, or phenenethyloxy group which may have one to three substituent(s), the substituent being selected from the group consisting of: C1–5 alkyl group and C1–3 alkoxy group; wherein R1 is —(CH2)17CH3, R2 is hydroxyl and R3 is hydrogen.

* * * * *

UNITED STATES PATENT AND TRADEMARK OFFICE
CERTIFICATE OF CORRECTION

PATENT NO. : 6,783,774 B1
DATED : August 31, 2004
INVENTOR(S) : Leslie Binshyang Song It is certified that error appears in the above-identified patent and that said Letters Patent is hereby corrected as shown below:

Title page,
Item [12], "Soong" should read -- Song --;
Item [54], Title, should read -- SUBSTANCES THAT STOP BLEEDING ON CONTACT FOR MEDICAL, SURGICAL, POST SURGICAL AND DENTAL USES --.
Item [75], Inventors, "Leslie Binshyang Soong" should read -- Leslie Binshyang Song --;

Column 8,
Lines 13-16, replace claims 2 and 3 with the following:
-- 2. The method of claim 1 wherein powdered D, L-threo-hex-2-enono-1.4-lactone and excipients are in a liquid form.
  3. The method of claim 1 wherein powdered D, L-threo-hex-2-enono-1,4-lactone and excipients are in a capsule form. --.

Signed and Sealed this

Thirty-first Day of January, 2006

JON W. DUDAS
*Director of the United States Patent and Trademark Office*

UNITED STATES PATENT AND TRADEMARK OFFICE
CERTIFICATE OF CORRECTION

PATENT NO. : 6,783,774 B1
DATED : August 31, 2004
INVENTOR(S) : Leslie Binshyang Song It is certified that error appears in the above-identified patent and that said Letters Patent is hereby corrected as shown below:

<u>Title page,</u>
Item [12], "Soong" should read -- Song --;
Item [54], Title, should read -- SUBSTANCES THAT STOP BLEEDING ON CONTACT FOR MEDICAL, SURGICAL, POST SURGICAL AND DENTAL USES --.
Item [75], Inventors, "Leslie Binshyang Soong" should read -- Leslie Binshyang Song --;

<u>Column 8,</u>
Lines 13-16, replace claims 2 and 3 with the following:
-- 2. The method of claim 1 wherein powdered D, L-threo-hex-2-enono-1,4-lactone and excipients are in a liquid form.
  3. The method of claim 1 wherein powdered D, L-threo-hex-2-enono-1,4-lactone and excipients are in a capsule form. --.

This certificate supersedes Certificate of Correction issued January 31, 2006.

Signed and Sealed this

Ninth Day of May, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,783,774 B1 |
| APPLICATION NO. | : 08/354653 |
| DATED | : August 31, 2004 |
| INVENTOR(S) | : Leslie Binshyang Song |

It is certified that error appears in the above-identified patent and that said Letters Patent is hereby corrected as shown below:

Col. 8, Lines 8-12, claim 1 should read

1. A method for stopping bleeding at a bleeding site, comprising administering topically to the bleeding site the effective dose of powdered L-threo-hex-2-enono-1,4-lactone and / or pharmaceutical excipients.

Col. 8, Lines 13-14, claim 2 should read

2. The method of claim 1, wherein the powdered L-threo-hex-2-enono-1,4-lactone and / or pharmaceutical 6excipients are to stop operational bleeding, post operational bleeding, including nose bleed, injured bleeding, intestinal or colon cancer bleeding, prostate carcinoma bleeding or other tumor bleeding, hemophilia bleeding, liver disease bleeding, peptic ulcer bleeding, extraction of teeth bleeding, scalp tumor excision bleeding, arterial-venous fistula plasty surgery bleeding for hem dialysis, skin graft operation bleeding, anal abscess operation bleeding, adenoid removal bleeding, pharyngeal operation bleeding, OB & GYN surgery bleeding etc. and veterinary hospital operational or post operational bleeding.

Signed and Sealed this

Twelfth Day of August, 2008

JON W. DUDAS
*Director of the United States Patent and Trademark Office*